US011141605B2

(12) United States Patent
Liu et al.

(10) Patent No.: US 11,141,605 B2
(45) Date of Patent: Oct. 12, 2021

(54) RADIOTHERAPY SYSTEM

(71) Applicant: OUR UNITED CORPORATION, Shaanxi (CN)

(72) Inventors: Haifeng Liu, Shaanxi (CN); Shiqun Xiao, Shaanxi (CN); Qi Gao, Shaanxi (CN)

(73) Assignee: OUR UNITED CORPORATION, Shaanxi (CN)

( * ) Notice: Subject to any disclaimer, the term of this patent is extended or adjusted under 35 U.S.C. 154(b) by 80 days.

(21) Appl. No.: 16/605,173

(22) PCT Filed: Apr. 17, 2017

(86) PCT No.: PCT/CN2017/080817
§ 371 (c)(1),
(2) Date: Oct. 14, 2019

(87) PCT Pub. No.: WO2018/191851
PCT Pub. Date: Oct. 25, 2018

(65) Prior Publication Data
US 2021/0138263 A1    May 13, 2021

(51) Int. Cl.
*A61N 5/10* (2006.01)

(52) U.S. Cl.
CPC ........ *A61N 5/10* (2013.01); *A61N 2005/1094* (2013.01); *A61N 2005/1096* (2013.01)

(58) Field of Classification Search
None
See application file for complete search history.

(56) References Cited

U.S. PATENT DOCUMENTS

| 4,506,155 A * | 3/1985 | Suzuki | G21F 5/015 |
| | | | 250/252.1 |
| 2005/0008121 A1* | 1/2005 | Low | A61N 5/1027 |
| | | | 378/65 |

(Continued)

FOREIGN PATENT DOCUMENTS

| CN | 201058183 Y | 5/2008 |
| CN | 101306232 A | 11/2008 |

(Continued)

OTHER PUBLICATIONS

International Search Report and Written Opinion for PCT/CN2017/080817, dated Dec. 28, 2017.

*Primary Examiner* — Hoon K Song
(74) *Attorney, Agent, or Firm* — Marshall, Gerstein & Borun LLP

(57) ABSTRACT

A radiotherapy system includes radiotherapy equipment and at least one source storage tank. The radiotherapy equipment includes a treatment head and a radioactive source component, the treatment head includes a first opening and an accommodation space, and the radioactive source component is located in the accommodation space of the treatment head; the source storage tank includes a tank body and a tank cover, the tank body includes a second opening and an accommodation space capable of accommodating the radioactive source component, and the tank cover is configured to close the second opening; the second opening of the source storage tank is connected to the first opening of the radiotherapy equipment, and the radioactive source component is movable between the treatment head and the source storage tank.

9 Claims, 2 Drawing Sheets

(56) References Cited

U.S. PATENT DOCUMENTS

2005/0035310 A1* 2/2005 Drobnik .................. G21F 5/015
250/506.1
2005/0224728 A1* 10/2005 Schwarz ................. G21F 5/018
250/506.1

FOREIGN PATENT DOCUMENTS

| CN | 101239224 B | 12/2010 |
| CN | 101645316 B | 12/2011 |

* cited by examiner

RADIOTHERAPY SYSTEM

CROSS-REFERENCE TO RELATED APPLICATION

This application is a national phase entry under 35 USC 371 of International Patent Application No. PCT/CN2017/080817 filed on Apr. 17, 2017, which is incorporated herein by reference in its entirety.

TECHNICAL HELD

The present disclosure relates to the field of medical instruments, and in particular, to a radiotherapy system.

BACKGROUND

Tumor is a common and frequently-occurring disease, and radiation therapy is a common treatment for tumor. Radiation therapy equipment utilizes radiations to penetrate through human tumors and kill tumor tissues so as to achieve a therapeutic purpose of treatment.

There are various ways to generate radiations in existing radiotherapy equipment, one of which is to generate radiations by radioactive nuclide decay, for example, using the decay of cobalt-60 to generate gamma rays. For radiotherapy equipment using radionuclides, in the prior art, before a radioactive source is installed, it is necessary to construct an operation room for shielding radiations by using shield blocks outside the radiotherapy equipment, and the operation room is commonly called a hot chamber. A radioactive source carrying lead tank and a pick-up device are placed in the hot chamber. By outdoor control operated outside the hot chamber, a hanging basket provided with the radioactive source is lifted from the lead tank by a lifting device and placed in a designated position of the hot chamber, and the radioactive source is filled into the radiotherapy equipment by the pick-up device. After the filling work is finished, the hot chamber constructed by the shield blocks is removed.

Since the shield blocks for constructing the hot chamber are made of heavy metal materials, the built space needs to accommodate the radioactive source carrying lead tank and the pick-up device, therefore, it is time-consuming, labor-intensive and difficult to construct and disassemble the hot chamber.

If the radiotherapy equipment fails during use, especially in a case where a treatment head fails, maintenance personnel need to enter the treatment room for maintenance. However, since the radioactive source cannot be easily removed, in a case where the maintenance personnel service the radiotherapy equipment, a radiation leakage may occur in the treatment head, which increases risk of radiation during maintenance of the maintenance personnel.

SUMMARY

Some embodiments of the present disclosure provide a radiotherapy system. In a case where the radiotherapy equipment is not used or the radiotherapy equipment is serviced, a radioactive source component may be shielded by a source storage tank to reduce the radiation risk of manual operation.

In order to solve the above technical problems, some embodiments of the present disclosure adopts the following technical solutions:

A radiotherapy system provided by the present application includes radiotherapy equipment and at least one source storage tank. The radiotherapy equipment includes a treatment head and a radioactive source component. The treatment head includes a first opening and an accommodation space, and the radioactive source component is located in the accommodation space of the treatment head.

The source storage tank includes a tank body and a tank cover, the tank body includes a second opening and an accommodation space capable of accommodating the radioactive source component, and the tank cover is configured to close the second opening.

The second opening of the source storage tank is configured to connect to the first opening of the radiotherapy equipment, and the radioactive source component is able to move between the treatment head and the source storage tank.

In the radiotherapy system provided by the present application, the source storage tank is fixedly disposed on the radiotherapy equipment;

The second opening includes a first sub-opening and a second sub-opening disposed oppositely, the first sub-opening is configured to connect the first opening of the radiotherapy equipment, and the tank cover is configured to close the second sub-opening.

In the radiotherapy system provided by the present application, the radiotherapy equipment includes two tank covers respectively configured to close the first sub-opening and the second sub-opening in one to one correspondence.

The radiotherapy system provided by the present application further includes a pull rod device. The pull rod device includes a pull rod and a first connection portion disposed on the pull rod; the pull rod extends into the source storage tank and drives the first connection portion to move in the source storage tank.

In the radiotherapy system provided by the present application, the tank cover is provided with a through hole, and the pull rod penetrates through the through hole and extends into the source storage tank, and drives the first connection portion to move in the source storage tank.

In the radiotherapy system provided by the present application, the radioactive source component is provided with a second connection portion, and the second connection portion is connected to the first connection portion.

In the radiotherapy system provided by the present application, the tank cover is movably connected to the tank body; or, the tank cover is able to move relative to the tank body.

In the radiotherapy system provided by the present application, the radiotherapy equipment further includes a push-pull device configured to move the radioactive source component.

In the radiotherapy system provided by the present application, the source storage tank is movable relative to the radiotherapy equipment.

In the radiotherapy system provided by the present application, the radioactive source component is provided with a first mating portion, the treatment head is provided with a second mating portion, and the first mating portion and the second mating portion are cooperatively fixed.

In the radiotherapy system provided by the present application, the treatment head further includes a closure member, and the closure member is configured to close the first opening.

In the radiotherapy system provided by the present application, the radiotherapy equipment further includes a fixed support, and the source storage tank is disposed on the fixed support.

In the radiotherapy system provided by the present application, the radiotherapy equipment further includes a roller, the roller is rotatable along its axis, and the treatment head is mounted on the roller.

In the radiotherapy system provided by the present application, the radiotherapy equipment includes two treatment heads, and each treatment head corresponds to one source storage tank respectively.

A radiotherapy system provided by the present disclosure includes radiotherapy equipment and at least one source storage tank. The radiotherapy equipment includes a treatment head and a radioactive source component, the treatment head includes a first opening and an accommodation space, and the radioactive source component is located in the accommodation space of the treatment head. The source storage tank includes a tank body and a tank cover, the tank body includes a second opening and an accommodation space capable of accommodating the radioactive source component, and the tank cover is configured to close the second opening. The second opening of the source storage tank is connected to the first opening of the radiotherapy equipment, so that in a case where the radiotherapy equipment or the treatment head needs to be serviced, the first opening is connected to the second opening, and the radioactive source component may be stored in the source storage tank to reduce the radiation risk of the operator's maintenance. Of course, the source storage tank may be further transferred to the outside of the treatment room and the like to further reduce the radiation risk of the operator's maintenance.

BRIEF DESCRIPTION OF THE DRAWINGS

In order to more clearly illustrate the embodiments of the present disclosure or the technical solutions in the prior art, the drawings used in the description of the embodiments or the prior art will be briefly described below. Obviously, the drawings in the following description are only a part of embodiments of the present disclosure, and those skilled in the art can obtain other drawings according to these drawings without any creative effort.

DETAILED DESCRIPTION

The technical solutions of the present disclosure are described in detail below with reference to the embodiments. Obviously, the described embodiments are merely some but not all of embodiments of the present disclosure. All other embodiments made on the basis of the embodiments of the present disclosure by a person of ordinary skill in the art without paying any creative effort shall be included in the protection scope of the present disclosure.

Figure 1:
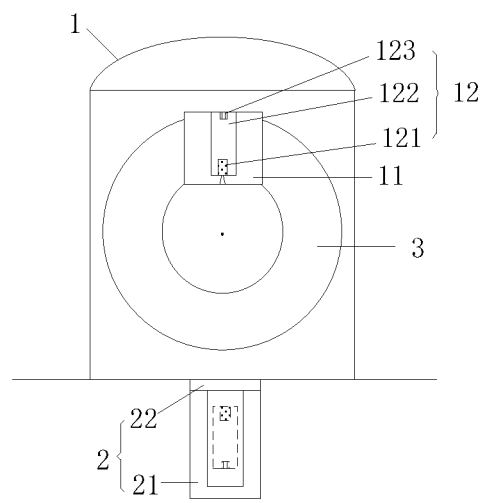
FIG. 1 is a diagram of a radiotherapy system according to some embodiments of the present disclosure.

A radiotherapy system provided by the present application, as shown in FIG. 1, includes radiotherapy equipment 1 and at least one source storage tank 2. As an example, FIG. 1 shows only one storage tank 2. The radiotherapy equipment 1 includes a treatment head 11 and a radioactive source component 12, the treatment head 11 includes a first opening and an accommodation space, and the radioactive source component 12 is located in the accommodation space of the treatment head 11; the source storage tank 2 includes a tank body 21 and a tank cover 22, the tank body 21 includes a second opening and an accommodation space capable of accommodating the radioactive source component 12, and the tank cover 22 is configured to close the second opening; the second opening of the source storage tank 2 is connected to the first opening of the radiotherapy equipment 1, so that the radioactive source component 12 is movable between the treatment head 11 and the source storage tank 2.

It should be noted that, the radiotherapy equipment uses a roller type as an example for description in the present application. In FIG. 1, the treatment head is disposed on a roller 3, and the treatment head 11 may be driven to do circular motion by the rotation of the roller 3. Of course, the present application does not limit the specific structure of the radio therapy equipment, but only illustrates the example shown in FIG. 1. For example, the radiotherapy equipment may also be a guide rail or a C-arm type.

In the present application, as shown in FIG. 1, the radioactive source component includes a radioactive source 121 and a source carrier body 122. In the present application, the source carrier body 122 may be formed of lead, tungsten or a tungsten alloy, and the source carrier body is in a shape of a strip. The carrier body is assembled on the treatment head to play a role of shielding rays. In the present application, the radioactive source component 12 further includes a second connection portion 123, and the second connection portion 123 may be an internal thread and may be threaded. Of course, the specific structure of the radioactive source component and the structure of the second connection portion are not specifically limited herein, and only the above is exemplified for illustration.

The positions of the source storage tank and the radiotherapy equipment are not specifically limited in the present application. For example, in FIG. 1, the source storage tank 2 is located below the radiotherapy equipment 1, and the radiotherapy equipment 1 may be located on the ground. An upper side of the source storage tank 2 is provided with a second opening, and the tank cover 22 is configured to close the second opening. The second opening is opened by moving the tank cover 22 so that the second opening is connected to the first opening of the treatment head.

In the present application, the second opening of the source storage tank 2 is connected to the first opening of the radiotherapy equipment 1, so that the radioactive source component 12 is movable between the treatment head 11 and the source storage tank 2. For example, as shown in FIG. 1, the roller may drive the treatment head 11 to rotate 180°, so that the first opening of the treatment head 11 is opposite to and connected to the second opening of the source storage tank 2, so that the radioactive source component is movable between the treatment head 11 and the storage tank 2. In a case where the radiotherapy equipment or the treatment head needs to be serviced, the radioactive source component may be accommodated in the source storage tank, so that the radioactive source component may be further transferred and the like to reduce the radiation risk of the operator's maintenance.

A radiotherapy system provided by the present application includes radiotherapy equipment and at least one source storage tank. The radiotherapy equipment includes a treatment head and a radioactive source component, the treatment head includes a first opening and an accommodation space, and the radioactive source component is located in the accommodation space of the treatment head; the source storage tank includes a tank body and a tank cover, the tank body includes a second opening and an accommodation space capable of accommodating the radioactive source component, and the tank cover is configured to close the second opening; the second opening of the source storage tank is connected to the first opening of the radiotherapy equipment, so that in a case where the radiotherapy equipment or the treatment head needs to be serviced, the first opening is connected to the second opening, and the radioactive source component may be stored in the source storage tank to reduce the radiation risk of the operator's maintenance. Of course, the source storage tank may be further transferred to the outside of the treatment room and the like to further reduce the radiation risk of the operator's maintenance.

In the radiotherapy system provided by the present application, the radioactive source component is provided with a first mating portion, the treatment head is provided with a second mating portion, and the first mating portion and the second mating portion are cooperatively fixed. For example, the first mating portion and the second mating portion may be matched by a buckle, a hook, and the like, so that the radioactive source component may be fixedly disposed on the treatment head. In some embodiments, the first mating portion and the second mating portion are matched by electronic devices, so that the first mating portion and the second mating portion may be remotely controlled to achieve a fixed connection of the radioactive source component and the treatment head.

Of course, in the radiotherapy system provided by the present application, the treatment head further includes a closure member configured to close the first opening to further prevent the radioactive source component from being disconnected from the treatment head. For example, the closure member may close the first opening by a hinge, by translation or the like. In some embodiments, the closure member closes the first opening by an electrical and electronic controller such that the closure member may be remotely controlled to close the first opening or open the first opening.

In the radiotherapy system provided by the present application, the radiotherapy equipment includes two treatment heads, and each treatment head corresponds to one source storage tank respectively; the two source storage tanks may be configured to store the radioactive source component of each treatment head respectively. For example, the two treatment heads may be a cobalt-60 focusing head and another may be a cobalt-60 conforming head. Or, both treatment heads may be cobalt-60 focusing heads, or both treatment heads may be cobalt-60 conforming heads. Of course, the radiotherapy equipment may also include more than two treatment heads, the treatment head may be a treatment head adopting an isotopic radiation source, and may further include an accelerator, etc., and the present application does not specifically limit the treatment head.

Figure 2:
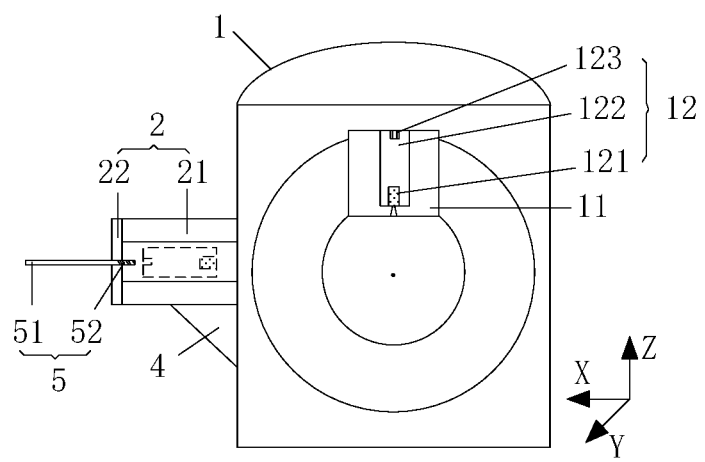
FIG. 2 is a diagram of another radiotherapy system according to some embodiments of the present disclosure.

In the radiotherapy system provided by the present application, as shown in FIG. 2, the source storage tank 2 is fixedly disposed on the radiotherapy equipment 1. In FIG. 2, the source storage tank 2 is fixedly disposed on the fixed support 4 as an example, and the fixed support 4 is fixed with the radiotherapy equipment 1. The second opening includes a first sub-opening and a second sub-opening disposed oppositely, wherein the first sub-opening is configured to connect the first opening of the radiotherapy equipment, and the tank cover 22 is configured to close the second sub-opening. Of course, the tank cover may also be two and configured to close the first sub-opening and the second sub-opening respectively.

Since the source storage tank is fixedly disposed on the radiotherapy equipment 1, the source storage tank includes two sub-openings, the first sub-opening is connected to the first opening of the radiotherapy equipment, so that the radioactive source component may enter the source storage tank from the first sub-opening, and the radioactive source component may also be removed from the second sub-opening.

Figure 3:
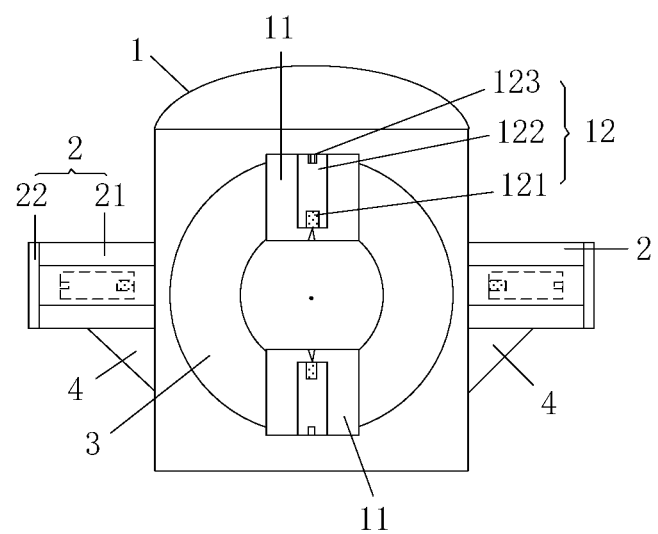
FIG. 3 is a diagram of yet another radiotherapy system according to some embodiments of the present disclosure.

For example, as shown in FIG. 2 and FIG. 3, the radiotherapy equipment 1 further includes a roller 3 and a fixed support 4 (part of the structure of the radiotherapy equipment 1 is shown in FIG. 2 and FIG. 3), the roller 3 is rotatable along its axis, and the treatment head 11 is mounted on the roller 3; the source storage tank 2 is fixedly connected to the fixed support 4. In FIG. 2 and FIG. 3, taking the source storage tank 2 being fixedly disposed on the fixed support 4 as an example, the fixed support 4 is fixedly connected to the radiotherapy equipment 1.

The tank cover of the radiotherapy system provided by the present application is movably connected to the tank body; or, the tank cover is movable relative to the rank body. For example, the tank cover is connected to the tank body by a hinge, or the movement of the tank cover may be achieved by a push-pull device. The move mode of the rank cover is not specifically limited in the present application, for example, the tank cover may be moved by an actuator driving a lead screw, or moved by an actuator driving a gear which is engaging with a ring. In addition, in the present application, the movement of the tank cover may be controlled by an electrical and electronic mode so that remote operation may be realized.

In some embodiments, the source storage tank is movable relative to the radiotherapy equipment. As shown in FIG. 2 and FIG. 3, the source storage tank 2 is fixedly disposed on the fixed bracket 4, and the fixed bracket 4 is movable relative to the radiotherapy equipment 1 along a z direction, thereby driving the source storage tank to move. Or, the source storage tank is also movable along an X or a Y direction relative to the fixed support 4.

The radiotherapy system provided by the present application, as shown in FIG. 2, further includes a pull rod device 5, and the pull rod device 5 includes a pull rod 51 and a first connection portion 52 disposed on a pull rod 51; the pull rod extends into the source storage tank and drives the first connection portion to move in the source storage tank.

For example, the tank cover 22 is provided with a through hole, and the pull rod 51 penetrates through the through hole and extends into the source storage tank 2, and drives the first connection portion 52 to move in the source storage tank 2. The pull rod 51 is able to penetrate through source storage tank and further extend into the treatment head, so that the first connection portion 52 of the pull rod is connected to the second connection portion 123 of the radioactive source component to transfer the radioactive source component from the treatment head to the source storage tank. Similarly, the radioactive source component in the source storage tank may also be fed into the treatment head.

In the present application, a connecting mode of the first connection portion and the second connection portion is threaded connection. The connection modes of the first connection portion and the second connection portion may be various, for example, an electromagnetic connection, etc., which is not limited in the present application.

In the present application, the movement of the pull rod may also be controlled by an electrical and electronic mode, so that the movement of the pull rod may be controlled remotely without manual operation.

In the radiotherapy system provided by the present application, the radiotherapy equipment further includes a push-pull device configured to move the radioactive source component, so as to move the radioactive source component into the source storage tank. That is, the transfer of the radioactive source component from the treatment head to the source storage tank is achieved. Similarly, the push-pull device may also pull the radioactive source component back into the treatment head, so that the source storage tank may be operated without the pull rod device. In some embodiments, the push-pull device may also be controlled by the electrical and electronic mode, thereby realizing remote operation.

In the description of the present disclosure, it will be understood that the orientation or positional relationship indicated by the terms "upper", "lower", "left", "right", "vertical", "horizontal", "top", "bottom", "inner", "outer" and so on is based on the orientation or positional relationship shown in the drawings, and is merely for the convenience of description of the present disclosure and simplification of the description, rather than indicating or implying that the device or the component must have a particular orientation, constructed and operation in a particular orientation, and thus cannot be construed as the limitation of the present disclosure. Moreover, the terms "first" and "second" are only used for describing purpose, rather than being interpreted as indicating or implying relative importance or implying and indicating the number of indicated technical features. Thus, the features defined with "first" and "second" may explicitly or implicitly comprise one or more of the features. In the description of the present disclosure, "a plurality of" means two or more than two, unless otherwise specified. Additionally, the terms "comprising", "including", and any deformation thereof are intended to cover a non-exclusive inclusion.

In the description of the present disclosure, unless specified or defined otherwise, it will be noted that the terms "mounted", "connected", "coupled" should be understood broadly, for example, a fixed connection, a detachable connection, or an integral connection; a mechanical or electrical connection; a direct connections or an indirect connection via intermediaries; an inner communications between two elements. The specific meanings of the above terms in the present disclosure can be understood by those ordinary skilled in the art according to specific situations.

The above description is only embodiments of the present disclosure, and thus does not limit the patent scope of the present disclosure. Any equivalent structure or equivalent process transformation, or directly or indirectly used in other related technical fields by the specification and the drawings content of the present disclosure, are all comprised in the scope of patent protection of the present disclosure.

What is claimed is:

1. A radiotherapy system, comprising a pull rod device, radiotherapy equipment and at least one source storage tank, wherein the pull rod device includes a pull rod and a first connection portion disposed on the pull rod; the pull rod extends into the source storage tank and drives the first connection portion to move in the source storage tank;

the radiotherapy equipment includes a fixed support, a treatment head and a radioactive source component, wherein the source storage tank is disposed on the fixed support, and then attached tightly to the radiotherapy equipment;

the treatment head includes a first opening and an accommodation space, and the radioactive source component is located in the accommodation space of the treatment head; and the radioactive source component includes a radioactive source, a source carrier body and a second connection portion; a connecting mode of the first connection portion and the second connection portion is threaded connection; the source carrier body is formed of lead, tungsten or a tungsten alloy;

the source storage tank includes a tank body and a tank cover, the tank body includes a second opening and an accommodation space capable of accommodating the radioactive source component, and the tank cover is configured to close the second opening; and the second opening of the source storage tank is configured to connect to the first opening of the radiotherapy equipment, and the radioactive source component is able to move between the treatment head and the source storage tank.

2. The radiotherapy system according to claim 1, wherein the second opening includes a first sub-opening and a second sub-opening disposed oppositely the first sub-opening is configured to connect the first opening of the radiotherapy equipment, and the tank cover is configured to close the second sub-opening.

3. The radiotherapy system according to claim 2, wherein the radiotherapy equipment includes two tank covers respectively configured to close the first sub-opening and the second sub-opening in one to one correspondence.

4. The radiotherapy system according to claim 1, wherein the tank cover is provided with a through hole, and the pull rod penetrates through the through hole and extends into the source storage tank, and drives the first connection portion to move in the source storage tank.

5. The radiotherapy system according to claim 1, wherein the tank cover is movably connected to the tank body; or, the tank cover is able to move relative to the tank body.

6. The radiotherapy system according to claim 1, wherein the radioactive source component is provided with a first mating portion, the treatment head is provided with a second mating portion, and the first mating portion and the second mating portion are cooperatively fixed.

7. The radiotherapy system according to claim 1, wherein the radiotherapy equipment includes two treatment heads, and each treatment head corresponds to one source storage tank respectively.

8. The radiotherapy system according to claim 1, wherein the treatment head further includes a closure member, and the closure member is configured to close the first opening.

9. The radiotherapy system according to claim 1, wherein the radiotherapy equipment further includes a roller, the roller is rotatable along its axis, and the treatment head is mounted on the roller.

* * * * *